United States Patent
Houston et al.

(10) Patent No.: US 6,776,194 B2
(45) Date of Patent: Aug. 17, 2004

(54) FLOW MEANS

(75) Inventors: John Graeme Houston, Perth (GB);
Peter Arno Stonebridge, Perth (GB);
John Bruce Cameron Dick,
Blarigowrie (GB); Robert Gordon Hood, Tayside (GB); Allana Johnstone, Dunblane (GB); Christophe Emmanuel Sarran, Perth (GB); Craig McLeod Duff, Tayside (GB); Allan Thomson, Paisley (GB)

(73) Assignee: Tayside Flow Technologies Limited, Dundee (GB)

( * ) Notice: Subject to any disclaimer, the term of this patent is extended or adjusted under 35 U.S.C. 154(b) by 0 days.

(21) Appl. No.: 10/164,105

(22) Filed: Jun. 5, 2002

(65) Prior Publication Data

US 2002/0179166 A1 Dec. 5, 2002

(30) Foreign Application Priority Data

Jun. 5, 2001 (GB) .............................................. 0113633

(51) Int. Cl.⁷ .............................................. F15D 55/00
(52) U.S. Cl. .......................... 138/39; 138/137; 138/110; 138/178; 138/108
(58) Field of Search .............................. 138/39, 37, 110, 138/108, 172, 178, 177, 176, 106, 129, 150, 154; 72/74, 114, 370.19, 59; 251/126

(56) References Cited

U.S. PATENT DOCUMENTS

| | | | | |
|---|---|---|---|---|
| 1,974,110 A | * | 9/1934 | Higley | 138/39 |
| 3,457,762 A | * | 7/1969 | Gain | 72/370.19 |
| 3,479,670 A | | 11/1969 | Medell | 623/1.33 |
| 3,503,246 A | * | 3/1970 | Shiokawa | 72/74 |
| 3,606,780 A | * | 9/1971 | Nagahara | 72/77 |
| 3,693,329 A | * | 9/1972 | Willis | 55/457 |
| 3,746,126 A | * | 7/1973 | de Cardenas | 181/227 |
| 3,750,444 A | * | 8/1973 | Bittner | 72/78 |
| 4,317,353 A | * | 3/1982 | Geppelt et al. | 72/299 |
| 4,377,083 A | * | 3/1983 | Shepherd et al. | 72/68 |
| 4,466,741 A | * | 8/1984 | Kojima | 366/339 |
| 4,514,997 A | * | 5/1985 | Zifferer | 72/68 |
| 4,747,697 A | * | 5/1988 | Kojima | 366/339 |
| 4,900,314 A | | 2/1990 | Quackenbush | 604/282 |
| 5,619,878 A | * | 4/1997 | Grosjean et al. | 72/56 |
| 5,649,951 A | | 7/1997 | Davidson | 606/198 |
| 5,653,745 A | * | 8/1997 | Trescony et al. | 623/1.29 |
| 5,992,465 A | * | 11/1999 | Jansen | 138/37 |
| 6,112,768 A | * | 9/2000 | Rath et al. | 138/39 |
| 6,442,838 B1 | * | 9/2002 | Mussler | 29/890.127 |
| 6,478,053 B2 | * | 11/2002 | Zanardi | 138/30 |

FOREIGN PATENT DOCUMENTS

| | | |
|---|---|---|
| EP | 0699424 | 3/1996 |
| EP | 1254645 A1 * | 6/2002 |
| GB | 0409528 | 5/1934 |
| GB | 0729618 | 5/1955 |
| GB | 2093943 | 9/1982 |
| GB | 2265959 | 10/1993 |
| GB | 2344053 | 5/2000 |
| WO | WO97/24081 | 7/1997 |
| WO | WO98/19632 | 5/1998 |
| WO | WO0038591 | 7/2000 |

* cited by examiner

*Primary Examiner*—Patrick Brinson
(74) *Attorney, Agent, or Firm*—Bracewell & Patterson, L.L.P.

(57) ABSTRACT

There is a disclosed a conduit supporting structure that imposes, maintains and/or reinforces a flow guiding formation of a conduit, whereby to effect a desired flow configuration in the conduit.

26 Claims, 4 Drawing Sheets

FLOW MEANS

CROSS-REFERENCE TO RELATED APPLICATIONS

This application claims the benefit of British patent application Serial No. 0113633.2, filed on Jun. 5, 2001.

TECHNICAL FIELD

This invention relates to means for effecting fluid flow patterns in conduits, particularly but not exclusively conduits such as blood flow tubing and stents, and other tubing carrying fluids essential to life or industrial fluids.

BACKGROUND OF THE INVENTION

WO00/38591 discloses conduits such as tubing and stents devised to induce helical flow in such a fashion as to eliminate or reduce turbulence and/or eliminate or reduce dead flow regions in the conduits. The conduit has internal helical grooving or ridging or other measures which induce such helical flow, taking into account the conduit dimensions and the viscosity and velocity of fluid.

External structures have been used to provide reinforcement of conduits (see for example U.S. Pat. Nos. 3,479,670 and 4,130,904), which may serve to protect the conduits from kinking or maintain conduits in an open positions but do not directly influence internal geometry of the conduit lumen. For example, in U.S. Pat. No. 3,479,670 the tube lumen remains smooth despite the presence of reinforcing polypropylene monofilaments wrapped around the tube.

In accordance with a first aspect of the present invention there is provided a conduit, adapted for flow of a fluid having characteristics and velocity and having a given diameter, by apparatus that imposes, maintains or reinforces a flow guiding formation internally of the conduit, the apparatus comprising a helical structure to cause helical, rotational flow eliminating or reducing turbulence and/or eliminating or reducing dead flow regions in the flow, when used for such a fluid flow.

In accordance with a second aspect of the invention, there is provided apparatus for forming a helical flow formation in a conduit, the apparatus comprising a helical structure, and being adapted to be engaged with a conduit for carrying a fluid, in use, such that the helical structure forms the helical flow formation inside the conduit, the angle of the helical flow formation being determined from the internal dimensions of the conduit, the fluid mass flow of the conduit, the pressure drop along the conduit and the turbulent kinetic energy within the conduit.

In accordance with a third aspect of the present invention, there is provided a method of determining the helix angle of a helical flow formation within a conduit, the method comprising specifying the internal dimensions of the conduit and an intended fluid mass flow through the conduit, and determining the helix angle from the pressure drop and the turbulent kinetic energy for a conduit having the specified internal dimensions and intended fluid mass flow.

Typically, the pressure drop and the turbulent kinetic energy are non-dimensionalized before the helix angle is determined.

Preferably, the helix angle is determined as the helix angle at which the non-dimensionalized pressure drop and the non-dimensionalised turbulent kinetic energy are substantially equal.

The helical flow formation may have a helix angle of between 5° and 50°. For example, the helical flow formation may have a helix angle of about 8°, particularly but not exclusively in relation to arterial flow in leg arterial grafts.

Typically, the fluid to be carried by the conduit comprises a liquid. The fluid may be a solely a liquid, a liquid mixed with a particulate solid, or a liquified solid. For example, where the conduit is blood vessel, the liquid is blood.

Preferably, the side wall of the conduit is deformable and the apparatus is engaged with the external side wall of the conduit such that the helical structure deforms the side wall of the conduit to form the helical flow formation on the interior of the conduit.

The helical flow formation may effect a rotational flow. The rotational flow may comprise a helical and/or spiral flow component.

The helical structure may comprise ridges which define a specific profile of the helical flow formation which effects the fluid flow pattern. Additionally or alternatively, the helical structure may comprise grooves which define a specific profile of the helical flow formation which effects the fluid flow pattern.

The helical flow formation may be orientated with a Z twist. A Z-twist orientation (also referred to as a right hand helix) creates clock-wise flow-inducing in the forward flow direction. Alternatively, the helical flow formation may be orientated with an S twist (also referred to as a left hand helix).

The apparatus may comprise symmetrical protrusions and/or asymmetrical protrusions, the asymmetrical protrusions having a gradually sloping leading edge and a steep sloping rear edge.

The apparatus may comprise single-start or multistart grooving and/or ridging.

The apparatus may comprise a frame. The frame may be formed by circular, rectangular, ovoid and/or differently parts. The frame may comprise parts having at least two different diameters.

The apparatus may comprise metals such as stainless steel. Alternatively or additionally, the structure may comprise synthetic or other thermoplastic or plastifiable material, being plastified and reset in twisted condition. Suitable materials include polytetrafluoroethylene (PTFE, also known as "Teflon"), polypropylene, nylon or other synthetic material. Stainless steel or other metallic structures maybe coated with synthetic or other thermoplastic or plastifiable material.

The apparatus may have a twisted appearance with an oval, rectangular or other non-circular cross-section. The structure may be coiled along its longitudinal axis and have a circular cross-section.

The apparatus may comprise patterned or solid material. The structure may be fixed or collapsable.

The helical flow formation may effect helical and/or spiral flow in such a fashion as to eliminate or reduce turbulence and/or eliminate or reduce dead flow regions in the conduit. Optimal helical angle to achieve such flow will depend on such factors as diameter of the conduit, longitudinal and rotational velocity of the fluid, and the viscosity and other characteristics of the fluid.

The apparatus may be branched.

The conduit may comprise tubing. For example, the conduit may comprise artificial or natural blood flow tubing, such as a graft or blood vessel, respectively. The tubing may be used in blood treatment or delivery equipment, for example a heat-lung machine, dialysis equipment or a giving set. The tubing may also be used in industrial equipment, for example hoses, pipes or fire hoses.

Alternatively, the conduit may comprise a stent. Stents, for example made of mesh, expanded sheet or tube or wire spring type, are inserted into blood vessels to provide mechanical support and prevent collapse of the blood vessel. A structure according to the present invention could be placed inside or outside the blood vessel to impose, maintain and/or reinforce a flow guiding formation through the blood vessel.

The invention may also be utilised for stent grafts, ie. a combination of stent and graft.

Also provided according to the present invention is a method for imposing, maintaining and/or reinforcing a helical flow formation which effects a desired flow configuration in a conduit, comprising fitting a support structure around the conduit wherein the structure imposes, maintains and/or reinforces the flow guiding formation.

Flow configuration through a conduit may, in general, be measured using such techniques MRI (magnetic resonance imaging) and/or Doppler ultrasound, and the flow guiding formation may be modified accordingly until a desired flow configuration is achieved. Initial design of flow configuration may be by mathematical modelling or by trial and error, with modification as described above.

BRIEF DESCRIPTION OF THE DRAWINGS

Examples of apparatus in accordance with the invention will now be described with reference to the accompanying drawings, in which.

DETAILED DESCRIPTION OF THE PREFERRED EMBODIMENT

The invention in general provides means and method for supporting precise internal surface architecture and configuration to induce a flow conformation, for example helical or rotational flow, thereby to improve fluid flow and reduce turbulence. Embodiments of structures encompassed by the present invention, and methods of manufacture thereof, are described below, although the invention is not intended to be limited by these examples. While the examples shown in certain cases relate to grafts or stent, the principles embodied therein also apply to other types of conduit.

Figure 1:
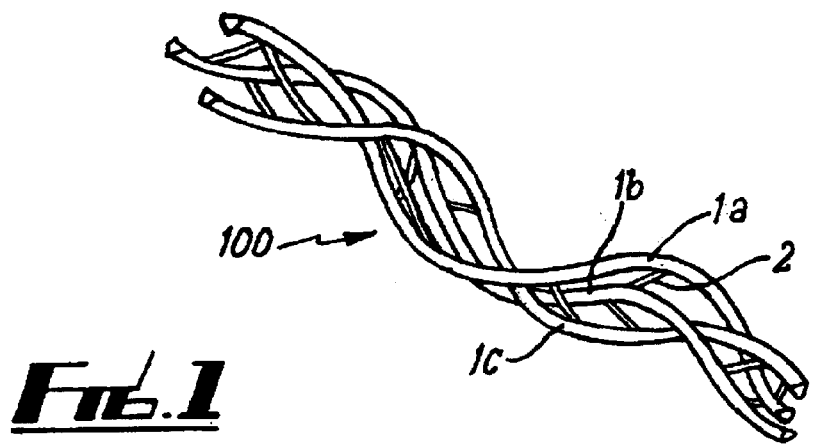
FIG. 1 is a perspective view of a plastics frame suitable for imposing a helical fluid flow.
Figure 2:
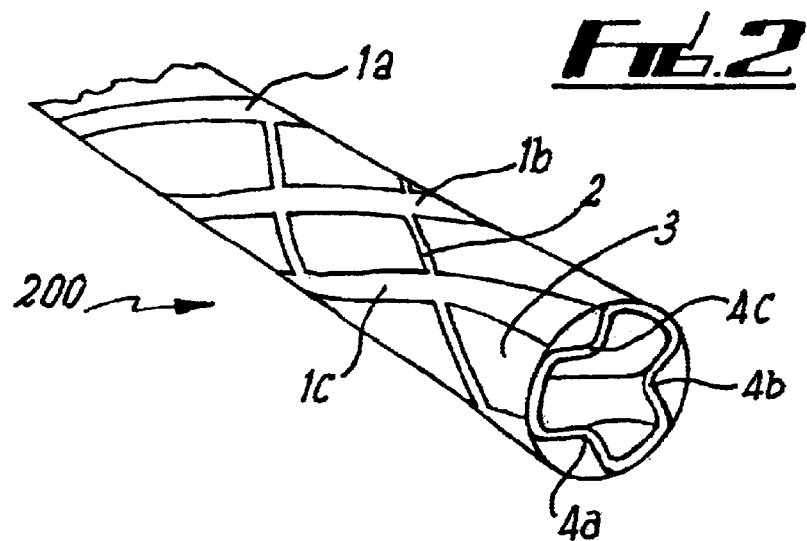
FIG. 2 is a perspective view of a frame as shown in FIG. 1 enclosing a graft.

FIG. 1 shows a helix structure 100 comprising ribs 1a–c which are disposed in a helical flow guiding formation along the longitudinal axis of the structure 100. Helix structure 100 further has smaller frame components (for example, connection 2) which support the orientation of the ribs 1a–c. Ribs 1a–c are more or less triangular in shape, with one of the edges of the triangle always facing the interior of the helix structure 100. With helix structure 100 is fitted over a graft 3, as shown generally at 200 in FIG. 2, ribs 1a–c impose groove formations 4a–c within the lumen of the graft 3, thereby effecting the helical flow guiding formation of the helix structure 100 with the graft 3.

In a preferred embodiment, helix structure 100 comprises polypropylene, but other synthetic material, metal and/or tissue engineered material may also be used. Graft 3 comprises PTFE material, which is sufficiently malleable to be shaped by ribs 1a–c. Other medical grade plastics or plastifiable material which has this malleable characteristic, for example Dacron, may also be used for graft 3.

Figure 3:
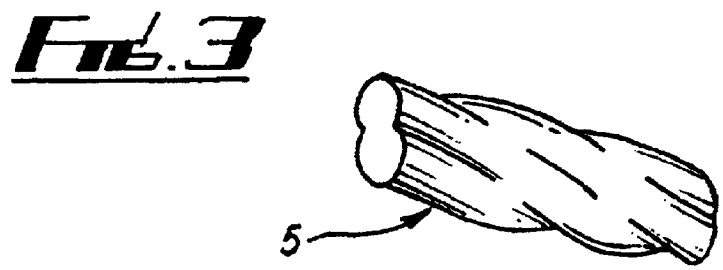
FIG. 3 is a perspective view of support structure with a spiralling ribbon conformation.

FIG. 3 shows a spiralling ribbon support structure 5. This structure, when fitted over a conduit, imposes or supports a double-barrelled helical flow pattern within the conduit. The helical flow pattern is effected by spiral orientation in the longitudinal axis of the structure.

Figure 4A:
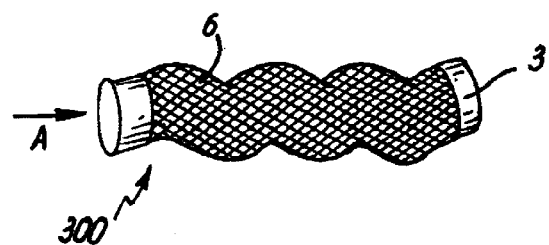
FIG. 4A is a perspective view of a wire mesh structure with a barley twist conformation enclosing a graft.
Figure 4B:
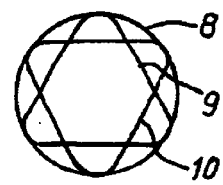
FIG. 4B shows the rotational effect of the structure depicted in FIG. 4A, as viewed in the direction of arrow A in FIG. 4A.

Shown generally at 300 in FIG. 4A is a barley twist conformation wire mesh 6 fitted over part of the length of a graft 3. In cross-section, mesh 6 imposes on graft 3 a shape which is approximately triangular. However, when viewed through one end in the direction of arrow A, as shown in FIG. 4B, graft 3 has a flow path with is circular through longitudinal axis (compacted view of circular path shown at 8) through sequential twisting of the approximately triangular cross-section shape of graft 3 (for example at stages 9 and 10). The mesh 6 thus imposes a helical flow pattern through graft 3 where mesh 6 is positioned over graft 3.

Figure 5:
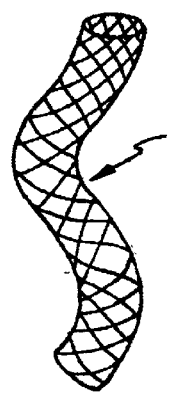
FIG. 5 is a perspective view of a mesh structure coiled along its longitudinal axis and having a circular cross-section.

Thus a helical flow path can be induced within a conduit by means of the conformation imposed by a structure along its longitudinal axis. Another example is shown in FIG. 5: longitudinally coiled mesh structure 11 has a circular cross-section throughout is conformed to induce upon a conduit within it a helical flow pattern. Grooves or ridges in the structure are not necessary to achieve the helical flow pattern in the example shown in FIG. 5.

Figure 6:
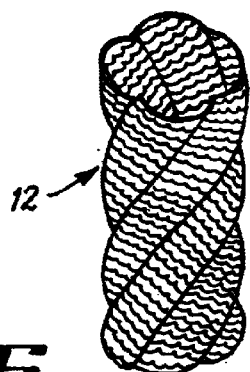
FIG. 6 is a perspective view a scaffold comprising French knitted Nitinol.

A French knitted Nitinol scaffold 6 is shown in FIG. 6. Cycling the pins in the manufacturing die results in the spiral knitted sock-like conformation of the scaffold 6. The scaffold is preferably manufactured from moulded polypropylene which is injected onto a Dacron graft with a heat sealing step to bond the plastic to the graft. The scaffold can also be manufactured from nylon. The scaffold can alternatively be manufactured as a dripcast or extruded synthetic frame.

The scaffold would be applied or compressed over a conduit, such as a graft of other blood flow tubing, to impose, maintain and/or reinforce a helical flow guiding formation within the conduit.

Figure 7A:
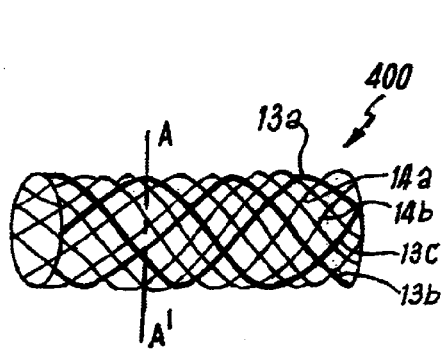
FIG. 7A is a perspective view of a mesh structure comprising wires with two different diameters.
Figure 7B:
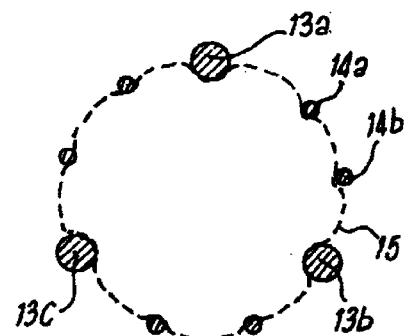
FIG. 7B is a cross sectional view through line A-A' in FIG. 7A.

In another embodiment depicted in FIG. 7A, a cylindrical wire mesh structure 400 comprises flow guidance forming wires 13a–c interspersed with support wires 14a,b which are orientated in the same direction and more or less parallel to the nearest flow guidance forming wire 13a–c. A flow guidance forming wire 13a–c would generally be thicker and more rigid than support wires 14a,b. When the cylindrical wire mesh structure 400 is fitted over a conduit, shown in conduit outline 15 in FIG. 7B, each flow guidance forming wire 13a–c imposes a ridge within the lumen of the conduit. It may be desirable that (smaller) ridges are also formed by support wires 14a,b within the conduit enclosed by the wire mesh structure 400—this would be dependent largely on the malleability of the conduit.

In modifications of the cylindrical wire mesh structure 400 shown in FIG. 7A, the wires need not be cylindrical but may be ovoid, rectangular, square, flat or other shapes. Wires used in wire mesh structures may be metallic or non-metallic and may also be coated. In the example shown in FIG. 7, there are three flow guidance forming wires 13a–c. However, the number of flow-inducing wires in this type of mesh structure may be one, two or more.

In yet another variation of the structure shown in FIG. 7, the material (metal, synthetic material, etc.) of different size and/or shape can be weaved and/or braided to form a conduit such that flow guidance forming patterns are formed within the conduit by the weaved or braided material. Here, the flow guidance forming patterns may be an integral component of the conduit, rather than external to the conduit. External structures may further be imposed over such weaved/braided conduits to support, enhance and/or form alternative flow guidance patterns within the conduit.

Figure 8A:
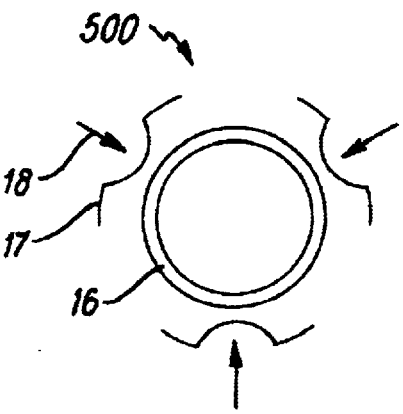
FIG. 8A is a cross-sectional view showing a method of construction of a structure.
Figure 8B:
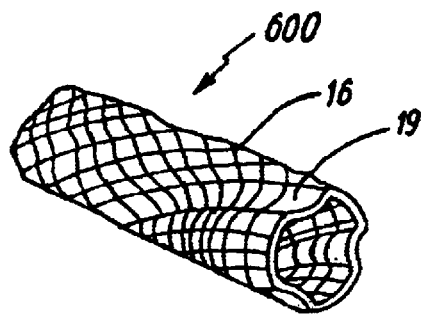
FIG. 8B is a perspective view of structure made according to the method shown in FIG. 8A.

Further examples of structures according to the present invention and their method of manufacture are shown in FIGS. 8–10. FIG. 8A shows in cross-section a modification 500 of a pre-formed Nitinol cylindrical mesh 16 by imposing a clamp 17 onto the Nitinol cylindrical mesh 16 in the direction of arrow 18 to create three grooves (with or without a thermal memory induction step). FIG. 8B depicts the Nitinol cylindrical mesh 16 after modification 500, where each groove 18 is orientated in a helical conformation around the Nitinol cylindrical mesh 16. The modified structure 600 can be fitted over a conduit to impose, maintain and/or reinforce a helical flow configuration. The Nitinol cylindrical mesh 16 may be alternatively be a Nitinol cut tube or a stainless steel cut tube.

Figure 9A:
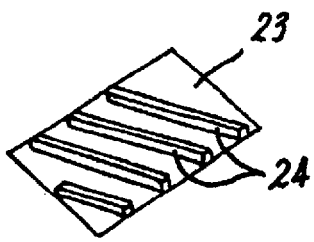
FIG. 9A is a perspective view of a plate with strips, for use in the manufacture of a structure.
Figure 9B:
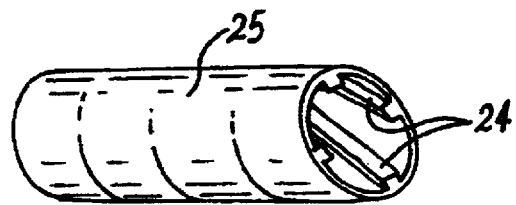
FIG. 9B is a perspective view of a structure made using the plate shown in FIG. 9A.

An alternative method of construction of a structure is shown in FIGS. 9A and 9B. Here, a plate 23 has rectangular bars 24 moulded, punched or attached thereto in a specific orientation (FIG. 9A). The plate 23 is rolled into a cylinder to form a ribbed cylinder 25 wherein the bars 24 form flow guiding profiles which, when the ribbed cylinder 25 is fitted over a conduit, impose, maintain and/or reinforce a flow guiding formation in the lumen of the conduit.

Figure 10A:
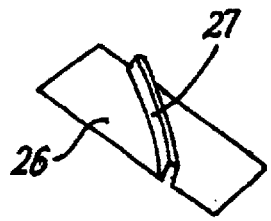
FIG. 10A is a perspective view of a plate having a raised spline, for use in the manufacture of a structure.
Figure 10B:
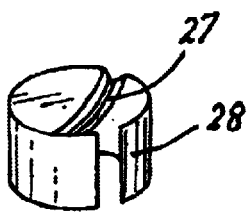
FIG. 10B is a perspective view of a structure made using the plate shown in FIG. 10A.

FIG. 10A shows a Nitinol strip 26 with a raised spline 27. When the Nitinol strip 26 is rolled into a cylinder conformation, as shown in FIG. 10B, spline 27 forms a flow guiding profile in the interior of the splined cylinder 28. Note that the rolled edges of splined cylinder 28 are not completely joined, which may be desirable for facilitating release or removal of the structure from a conduit. Naturally, alternative materials other than Nitinol will be amenable to these methods for forming structures according to the invention.

Structures according to the present invention can impose, maintain and/or reinforce a flow guiding formation of a conduit in a temporal manner, for example during pulsate blood flow through a blood flow tubing. The structures may be placed over natural ("native") blood vessels such as arteries or veins to impose, maintain and/or reinforce a flow guiding formation in situ as the blood vessel dilates. In certain cases, use of artificial grafts may be avoided. The structures may also be placed over previously implanted grafts or conduits to impose, maintain and/or reinforce a flow guiding formation.

The choice of the helix angle of the helical flow formation is important in minimizing turbulent flow and dead spots within the flow. The inventors have found that for a conduit having a given internal dimensions and a particular helical flow formation that is intended to carry a given mass flow, the optimum helix angle can be determined from the pressure drop along the conduit and the turbulent kinetic energy in the conduit.

Figure 11:
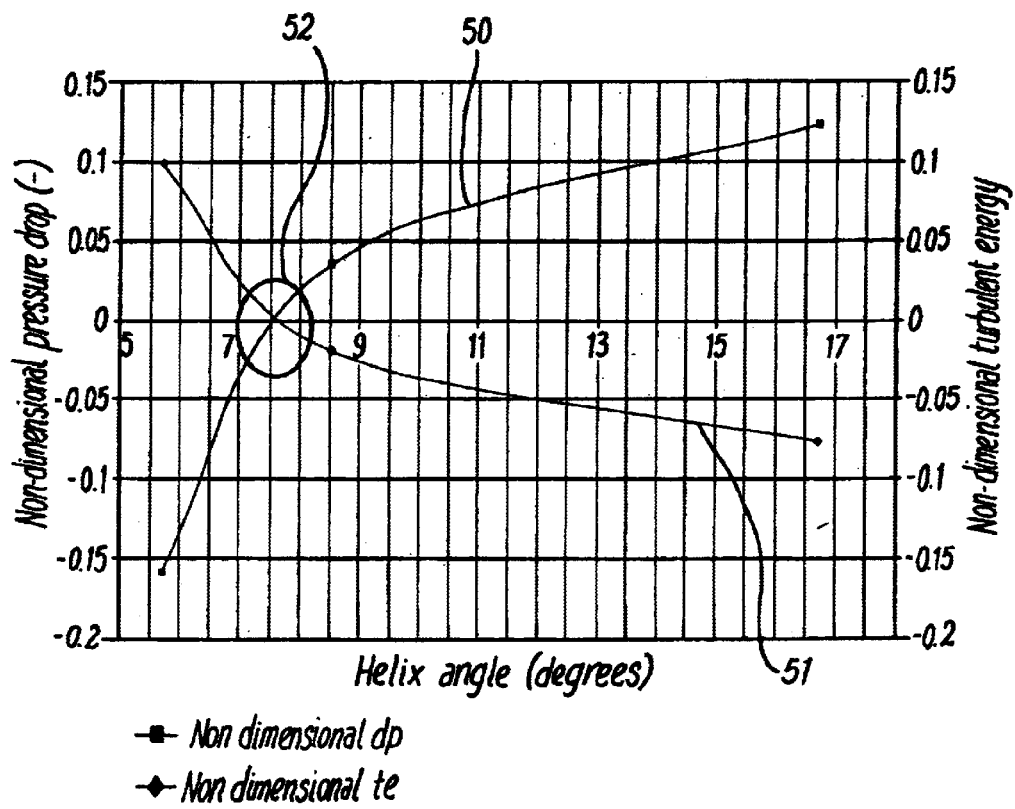
FIG. 11 is a graph of helix angle versus pressure drop and helix angle versus turbulent kinetic energy for an arterial blood vessel.

The inventors have found that in order to maintain a given mass flow in a given conduit, with a particular helical flow formation, the pressure drop increases as the helix angle increases and the turbulent kinetic energy decreases as the helix angle increases. Hence, the choice of helix angle is a compromise between minimising pressure drop and minimising turbulent kinetic energy. If the pressure drop and turbulent kinetic energy are non-dimensionalised using conventional mathematical techniques, the curves of helix angle versus non-dimensionalised pressure drop and helix angle versus turbulent kinetic energy can be plotted on the same graph. A curve 50 of helix angle versus non-dimensionalised pressure drop and a curve 51 of helix angle versus non-dimensionalised turbulent kinetic energy for an arterial graft are shown in FIG. 11. These curves 50, 51 were obtained from measuring pressure drop and turbulent kinetic energy in the arterial graft using conventional techniques. The curves 50, 51 show that at the region 52, the curves intersect and this intersection occurs at a helix angle of approximately 8°.

By also analysing flow in the graft using conventional magnetic resonance imaging techniques it was found by trial and error that the optimum helix angle for the graft for the given mass flow was also approximately 8°. Hence, the optimum helix angle for the graft occurs at approximately when the non-dimensionalised pressure drop is approximately equal to the non-dimensionalised turbulent kinetic energy.

The present invention is also suitable for industrial applications. Structures may be imposed upon conduits such as tubes to create improved efficiency through quicker transfer of fluid and reduced energy use or a reduction in pressure gradient along the tube allowing lower pressures within the tube to deliver a specific end conduit pressure/flow rate. Structures could effect a reduction in turbulence, thereby reducing vibration, noise, and/or fatigue in a conduit, which in pumps could allow for reduced pump power consumption. . Structures may allow further penetration or more accurate distribution patterns of fluid exiting a conduit, for example from a hose pipe for domestic use or from a fire hose. The invention will also be of benefit to industries where slurries or suspensions are transported through conduits, for example food producers or distributors involved with soups, sauces and like products.

As with the example above of the graft, the optimum helix angle for these other types of conduits can be determined from the pressure drop and the turbulent kinetic energy.

Therefore, the invention has the advantage of enabling the helix angle of a helical flow formation in a given size of conduit intended to carry a given fluid to be determined from the pressure drop and the turbulent kinetic energy in the conduit.

We claim:

1. Apparatus for forming a helical flow formation in a conduit, the apparatus comprising a helical structure, and being adapted to be engaged with a conduit for carrying a fluid, in use, such that the helical structure forms the helical flow formation inside the conduit, the angle of the helical flow formation being determined from the internal dimensions of the conduit, the fluid mass flow of the conduit, the pressure drop along the conduit and the turbulent kinetic energy within the conduit; and wherein the apparatus is external of the conduit.

2. A method of determining the helix angle of a helical flow formation having a pressure drop and a turbulent kinetic energy within a conduit, the method comprising specifying the internal dimensions of the conduit and an intended fluid mass flow through the conduit, and determining the helix angle from the pressure drop and the turbulent kinetic energy for a conduit having the specified internal dimensions and intended fluid mass flow.

3. A method according to claim 2, wherein the pressure drop and the turbulent kinetic energy are non-dimensionalised before the helix angle is determined.

4. A method according to claim 3, wherein the helix angle is determined as the helix angle at which the non-dimensionalised pressure drop and the non-dimensionalised turbulent kinetic energy are substantially equal.

5. Apparatus for generating rotational flow of a fluid in a conduit, the apparatus comprising a conduit and a structure for the conduit, the structure being placed externally around the conduit in use, and the structure comprising conduit deforming means, the conduit deforming means deforming the side walls of the conduit such that, the deformation of the side walls forms a helical formation within the conduit that generates rotational flow in a fluid flowing through the conduit.

6. Apparatus according to claim 5, wherein the conduit deforming means comprises internal ridges which define a specific profile of the deformation of the internal side walls.

7. Apparatus according to claim 5, wherein the structure further comprises grooves which define a specific profile of the deformation of the internal side walls.

8. Apparatus according to claim 5, wherein the helical formation has a helical angle of between 50 and 50°.

9. Apparatus according to claim 5, wherein the structure comprises a single-start or multistart grooving and/or ridging.

10. Apparatus according to claim 5, wherein the structure comprises a frame.

11. Apparatus according to claim 10, wherein the frame is formed by circular, rectangular, ovoid and/or differently shaped parts.

12. Apparatus according to claim 10, wherein the frame comprises parts having at least two different diameters.

13. Apparatus according to claim 5, wherein the structure comprises stainless steel.

14. Apparatus according to claim 5, wherein the structure comprises synthetic or other thermoplastic or plastifiable material, being plastified and reset in twisted condition.

15. Apparatus according to claim 5, wherein the structure has a twisted appearance with an oval, rectangular or other non-circular cross-section.

16. Apparatus according to claim 5, wherein the structure is coiled along its longitudinal axis and has a circular cross-section.

17. Apparatus according to claim 5, wherein the structure comprises patterned or solid material.

18. Apparatus according to claim 5, wherein the structure is fixed or collapsible.

19. Apparatus according to claim 5, wherein the structure is branched.

20. Apparatus according to claim 5, wherein the conduit comprises tubing.

21. Apparatus according to claim 20, wherein the conduit comprises artificial or natural blood flow tubing.

22. Apparatus according to any claim 5, wherein the structure comprises a stent.

23. A method of generating rotational flow in a fluid flowing through a conduit, the method comprising placing a structure externally around the conduit, the structure comprising conduit deforming means that deform the side walls of the conduit when the structure is placed around the conduit in use, such that, the deformation of the side walls forms a flow guiding formation within the conduit that generates rotational flow in a fluid flowing through the conduit.

24. A method according to claim 23, wherein the rotational flow comprises helical flow.

25. A method according to claim 23, wherein the flow guiding formation comprises a helical formation.

26. A method according to any of claim 23, wherein the flow guiding formation comprises a helical deformation of the longitudinal axis of the conduit.

* * * * *